United States Patent [19]

Ponpipom et al.

[11] 4,189,471
[45] Feb. 19, 1980

[54] IMMUNOLOGIC GLYCOLIPID ADJUVANTS

[75] Inventors: Mitree M. Ponpipom, North Plainfield; John Chabala; Tsung-Ying Shen, both of Westfield, all of N.J.

[73] Assignee: Merck & Co., Inc., Rahway, N.J.

[21] Appl. No.: 923,520

[22] Filed: Jul. 11, 1978

[51] Int. Cl.$^2$ .......................... A61K 31/575; C07J 9/00
[52] U.S. Cl. ........................ 424/88; 424/182; 260/397.2; 536/5; 536/7; 536/4
[58] Field of Search .......... 424/182, 88; 536/5, 536/7; 260/397.2

[56] References Cited

U.S. PATENT DOCUMENTS

| | | | |
|---|---|---|---|
| 3,036,062 | 5/1962 | Belding et al. | 536/5 |
| 3,189,597 | 6/1965 | Belding et al. | 536/5 |
| 3,702,848 | 11/1972 | Van Rheenen | 260/397.2 |
| 3,715,350 | 2/1973 | Hamashima | 260/397.2 |
| 4,084,010 | 4/1978 | Takemoto et al. | 536/5 |

*Primary Examiner*—Johnnie R. Brown
*Attorney, Agent, or Firm*—Donald J. Perrella; Julian S. Levitt

[57] ABSTRACT

Glycolipid compounds of the formulae

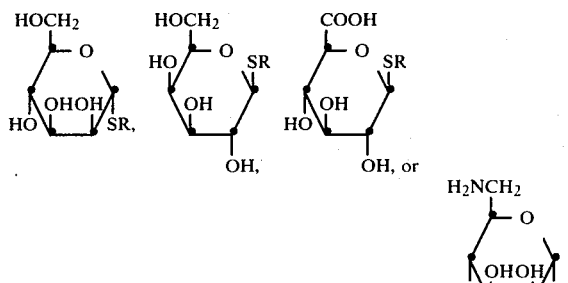

wherein R is

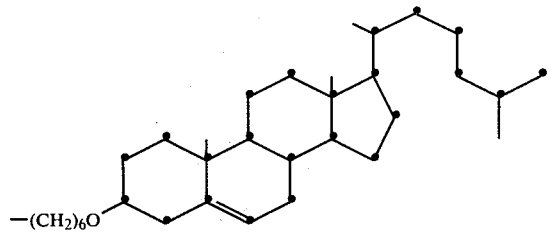

are useful immunologic adjuvants in vaccines.

4 Claims, No Drawings

IMMUNOLOGIC GLYCOLIPID ADJUVANTS

BACKGROUND OF THE INVENTION

The present invention relates to an immunologic adjuvant and, more particularly to novel glycolipid immunologic adjuvant and to improved vaccine formulations containing a novel glycolipid immunologic adjuvant.

Broadly considered, the vaccines utilized at the present time are "fluid vaccines." The term "fluid vaccine" designates a suspension of an immunogenic or desensitizing agent in water or in a medium comprising a single, aqueous, liquid phase. The principal purpose for employment of an immunologic adjuvant is to achieve a more durable immunity of a higher level employing a smaller antigenic mass in a fewer number of doses than could be achieved by administration of the equivalent aqueous antigen. It may be noted that development of an immunologically satisfactory and pharmacologically acceptable adjusvant is a prime essential for the preparation of workable multivalent killed virus vaccines which are effective and practical in the prevention of viral, bacterial, mycoplasmal or rickettsial diseases.

OBJECTS OF THE INVENTION

It is an object of the present invention to provide new glycolipid compounds. Another object is to provide methods for preparing these glycolipid compounds. A further object is to provide vaccine compositions containing these glycolipid compounds. These and other objects of the present invention will be apparent from the following description.

SUMMARY OF THE INVENTION

Glycolipid compounds of the formulae

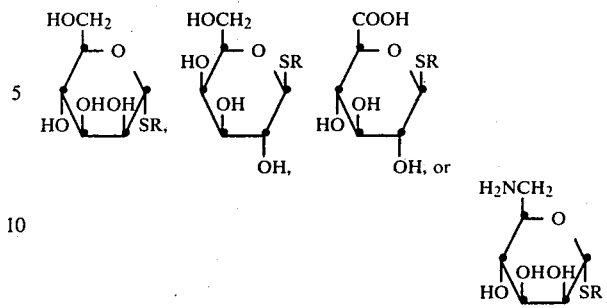

wherein R is

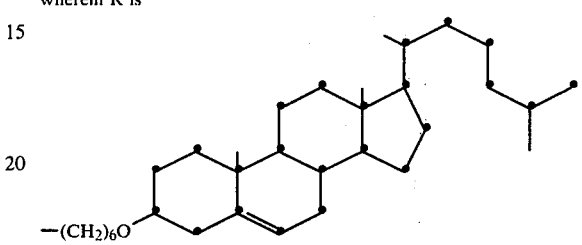

are useful immunologic adjuvants in vaccines.

DETAILED DESCRIPTION

The glycolipid compounds of the present invention which are useful as immunologic adjuvants are prepared with reference to Table I starting from cholesterol tosylate I. The latter may be condensed with hexanediol in an aprotic solvent such as, for example, dioxane or tetrahydrofuran (THF) to yield the corresponding 6-hydroxyhexyl derivative II. The latter may be converted to the 6-p-toluenesulfonyloxy derivative III using known methods, e.g. treatment with p-toluenesulfonic anhydride or a p-toluenesulfonyl halide. The latter may be converted to the corresponding 6-iodo derivative IV using known methods, e.g., by treatment with a metallic iodide, e.g. LiI or NaI. The

TABLE I

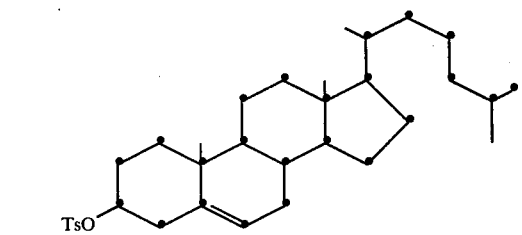

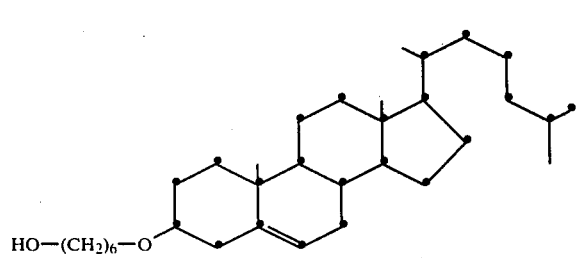

TABLE I-continued

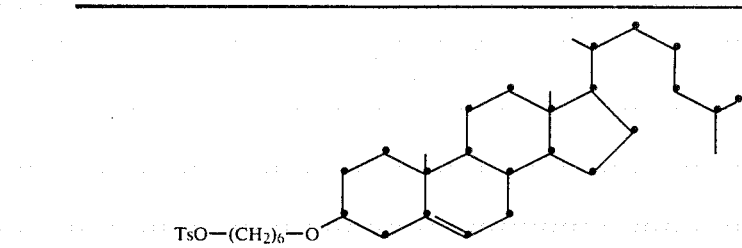

III

TsO—(CH₂)₆—O

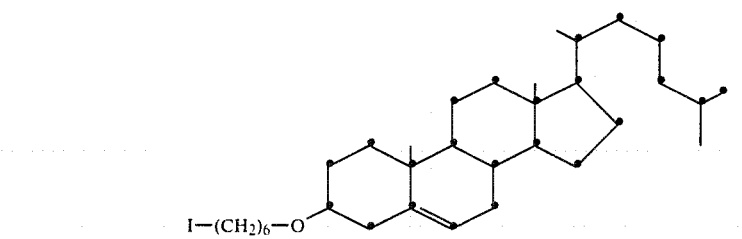

IV

I—(CH₂)₆—O

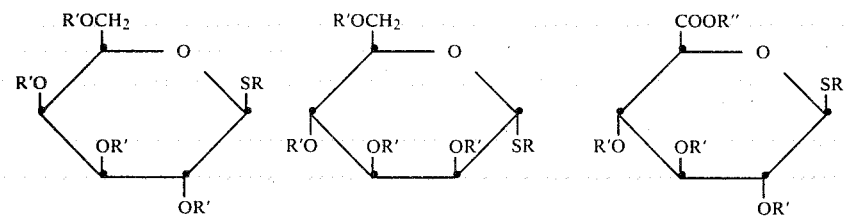

Va  R=H, R'=Ac
VIa  R=X, R'=Ac
VIIa R=X, R'=H

Vb  R=H, R'=Ac
VIb  R=X, R'=Ac
VIIb R=X, R'=H

Vc  R=H, R'=Ac, R''=CH₃
VIc  R=X, R'=Ac, R''=CH₃
VIIc R=X, R'=R''=H

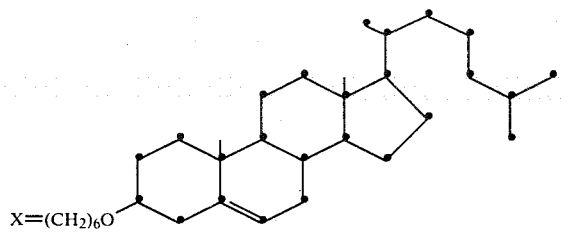

X=(CH₂)₆O protected compounds of formula VI a-c may be obtained by reacting IV with Va-c. This reaction takes place in an aprotic solvent, preferably a halogenated aprotic solvent, such as, for example, CH₂Cl₂, CHCl₃, CCl₄, acetonitrile or benzene, and in the presence of an acid acceptor such as, for example, triethylamine (TEA) or 1,5-diazabicyclo [5,4,0]undec-5-ene. The final products of formula VII a-c may be obtained by deprotecting the compounds of formula VI a-c. This may be accomplished using known methods by saponification in the presence of a base such as, for example, NaOCH₃, NH₃, or an anionic ion exchange resin.

The final product of formula VII d may be obtained with reference to Table 2 starting from 1-1,2,3,4-tetra-O-acetyl-6-O-methylsulfonyl-D-mannose VIII and converting the latter to the corresponding α-glycosyl bromide IX by bromination using known methods such as, for example, treatment with HBr in glacial acetic acid. The latter may be converted to the corresponding isothiouronium bromide X using known methods such as, for example, treatment with thiourea in a polar solvent such as, for example, acetone, methylethyl ketone (MEK) or dimethylformamide (DMF), at a temperature about equal to the boiling point of the solvent. The isothiouronium bromide X may be converted to the corresponding thiol XI using known methods such as, for example, treatment with K₂S₂O₅ in an aprotic solvent, preferably a halogenated solvent, such as, for example, CHCl₃ or CH₂Cl₂ at a temperature about equal to the boiling point of the solvent. The thiol in turn may be coupled with IV using the conditions previously described to yield the compound of formula XII. The latter may be converted to the

TABLE 2

R''CH₂
     \
      O
R'O  OR'  R'O  R

| | |
|---|---|
| VIId | R=SX, R'=H, R''=NH₂ |
| VIII | R=OAc, R'=Ac, R''=OMs |
| IX | R=Br, R'=Ac, R''=OMs |
| X | R=SC(=NH₂⁺)NH₂Br⁻, R'=Ac, R''=OMs |
| XI | R=SH, R'=Ac, R''=OMs |
| XII | R=SX, R'=Ac, R''=OMs |
| XIII | R=SX, R'=Ac, R''=N₃ |
| XIV | R=SX, R'=H, R''=N₃ |

TABLE 2-continued

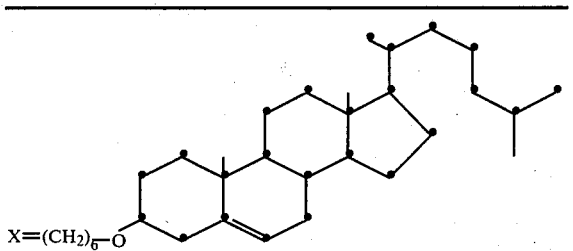

X=(CH₂)₆–O the azide of formula XIII using known methods for example, by treatment with NaN₃ in a polar solvent such as, for example DMF, acetone or MEK. The protected compound of formula XIII may be deblocked using the conditions previously described to prepare the compound of formula XIV which then may be converted to the final amino product of formula VIId using known methods such as, for example, by treatment with H₂S.

The novel adjuvants of the invention may be employed to potentiate the antibody response of antigenic materials. The term "antigen" and "antigenic material" which are used interchangeably herein include one or more non-viable immunogenic or desensitizing (antiallergic) agents of bacterial, viral or other origin. The antigen component of the products of the invention may consist of a dried powder, an aqueous solution, an aqueous suspension and the like, including mixtures of the same, containing a non-viable immunogenic or desensitizing agent or agents.

The aqueous phase may conveniently be comprised of the antigenic material in a parenterally acceptable liquid. For example, the aqueous phase may be in the form of a vaccine in which the antigen is dissolved in a balanced salt solution, physiological saline solution, phosphate buffered saline solution, tissue culture fluids or other media in which the organism may have been grown. The aqueous phase also may contain preservatives and/or substances conventionally incorporated in vaccine preparations. The adjuvant emulsions of the invention may be prepared employing techniques well known to the art.

The antigen may be in the form of purified or partially purified antigen derived from bacteria, viruses, rickettsia or their products, or extracts of bacteria, viruses, or rickettsia, or the antigen may be an allergen such as pollens, dusts, danders, or extracts of the same or the antigen may be in the form of a poison or a venom derived from poisonous insects of reptiles. In all cases the antigens will be in the form in which their toxic or virulent properties have been reduced or destroyed and which when introduced into a suitable host will either induce active immunity by the production therein of antibodies against the specific microorganisms, extract or products of microorganisms used in the preparation of the antigen, or, in the case of allergens, they will aid in alleviating the symptoms of the allergy due to the specific allergen. The antigens can be used either singly or in combination; for example, multiple bacterial antigens, multiple viral antigens, multiple mycoplasmal antigens, multiple rickettsial antigens, multiple bacterial or viral toxoids, multiple allergens or combinations of any of the foregoing products can be combined in the aqueous phase of the adjuvant composition of this invention. Antigens of particular importance are derived from bacteria such as *B. pertussis, Leptospira pomona* and *icterohaemorrhagiae, S. typhosa, S. paratyphi A* and *B, C. diphtheriae, C. tetani, C. botulinum, C. perfringens, C. feseri* and other gas gangrene bacteria, *B. anthracis, P, pestis, P. multocida, V. cholerae, Neisseria meningitidis, N, gonorrheae, Hemophilus influenzae, Treponema pollidum*, and the like; from viruses as polio virus (multiple types), adeno virus (multiple types), parainfluenza virus (multiple types), measles, mumps, respiratory syncytial virus, influenza (various types), shipping fever virus (SF₄), Western and Eastern equine encephalomyelitis, Japanese B. encephalomyelitis, Russian Spring Summer encephalomyelitis, hog cholera virus, Newcastle disease virus, fowl pox, rabies, feline and canine distemper and the like viruses, from rickettsiae as epidemic and endemic typhus or other members of the spotted fever group, from various spider and snake venoms or any of the known allergens for example from ragweed, house dust, pollen extracts, grass pollens and the like.

The following examples illustrate the present invention without, however, limiting the same thereto.

EXAMPLE 1

Preparation of Cholest-5-en-3α-yl 6-hydroxyhexyl Ether (II)

Using the procedure of Davis, J. Chem. Soc. 178–181 (1962), cholesterol tosylate and 1,6-hexanediol were condensed in refluxing dioxane to provide 52% yield of the title ether as colorless plates from hexane, m.p. 79.5°–81° C.; $[\alpha]_D^{25} -28.1° \pm 0.5°$ C.; IR 3500–3200 (OH), 1100 and 1080 cm$^{-1}$ (ether); NMR (CDCL₃): δ2.8-3.3 (br, 1H, H-1), 3.3-3.75 (2t,4H), 5.4 m, 1H).

Anal. Calc. for $C_{33}H_{58}O_2$: C, 81.42; H, 12.01. Found: C, 81.74; H, 11.78.

EXAMPLE 2

Preparation of Cholest-5-en-3α-yl 6-iodohexyl Ether IV

The alcohol, prepared by the process of Example 1 (16.0 g, 32.9 mmol) in 650 ml. dry benzene was treated with 11.9 g (36.3 mmol) p-toluenesulfonic anhydride prepared by the process of L. Field and J. W. McFarland, *Org. Syn. Coll.*, Vol. IV (1963) 940-942, and 5.8 ml (36 mmol) collidine, and stirred 1 hour at room temperature with the exclusion of moisture. The mixture was filtered through Florisil and concentrated to 16.0 g (76%) waxy cholest-5-en-3β-yl 6-(p-tolylsulfonyloxy) hexyl ether (III), homogeneous on TLC (15% EtOAc in benzene on silica gel); IR 1189 and 1175 (sulfonate), 1092 and 1087 (ether) cm$^{-1}$; NMR (CDCl₃):δ 2.43 (s, 3H), 2.7-3.3 (m, overlapping t, 3H), 3.90 (t, 2H), 5.3 (m, 1H), 7.24 and 7.70 (d of d, 4H). This tosylate (14.2 g, 22.2 mmol) and 7.0 g. (47 mmol) NaI were refluxed together for 4 hours in 120 ml acetone. Solvent was removed under reduced pressure. The residue was treated with 75 ml ether, filtered, and the collected salts washed well with ether. The filtrate was evaporated and the residual yellow oil boiled with 200 ml hexane. The solution was decanted, concentrated to 100 ml, and refrigerated 2 days, depositing 9.85 g white needles. A second crop afforded 2.90 g (total yield: 12.75 g, 97%), m.p. 103.5°–104.5° C.; $[\alpha]_D^{25} -22.6 \pm 0.5$ (c=1.02 CHCl₃); IR 1105 (ether) cm$^{-1}$.

Anal. Calc. for $C_{33}H_{57}IO$: C, 66.42; H, 9.63. Found: C, 66.32; H, 9.55.

EXAMPLE 3

Preparation of Glycosyl thiols 2,3,4,6-Tetra-O-acetyl-1-thio-β-D-galactopyranose (Va) was prepared by the process set forth in M. Cerny, J. Stanek, and J. Pacak, Monatsh., 94 (1963) 290-294 and 2,3,4,6-tetra-O-acetyl-1-thio-1-α-D-mannopyranose (Vb) was prepared using the procedure set forth in K. L. Matta, R. N. Girotra, and J. J. Barlow, *Carbohydrate Res.*, 43 (1975) 101-109.

Methyl 2,3,4-tri-O-acetyl-1-thio-β-D-glucopyranosuronate (Vc) was prepared from the bromide described in W. D. S. Bowering and T. E. Timell, *J. Am. Chem. Soc.*, 82 (1960) 2827-2830 according to the method set forth in M. Cerny, J. Stanek and J. Pacak, Monatsh., 94, 290-294 (1963), requiring the use of 2-butanone for the preparation of the intermediate isothiouronium bromide. Needles, m.p. 129.5°-130° C.; $[\alpha]_D^{25} -4.2° \pm 0.5°$ (c 1.0 CHCl$_3$); IR 2550 (thiol), 1740 (acetate) cm$^{-1}$; NMR (CDCl$_3$): δ 2.03 (s, 6H), 2.10 (s, 3H), 2.33 (d, J 10 Hz, 1H), 3.78 (s, 3H).

Anal. Calc. for C$_{13}$H$_{18}$O$_9$S: c, 44.57; H, 5.18; S, 9.15. Found: c, 44.41; H, 4.97; S, 8.94.

EXAMPLE 4

Preparation of Protected Glycolipids

To a solution of 1 equivalent glycosyl thiol in CH$_2$Cl$_2$ (20 ml per g thiol) was added 1 equivalent cholest-5-en-3β-yl 6-iodohexyl ether (IV) and 1 equivalent triethylamine. After stirring under N$_2$ at room temperature overnight, the mixture was chromatographed on silica gel using gradient elution with 5-25% ethyl acetate in benzene to yield the following compounds:

6-(Cholest-5-ene-3β-yloxy)hexyl 2,3,4,6-tetra-O-acetyl-1-thio-α-D- mannopyranoside (VIb)

55%, needles, m.p. 103°-105° C. (from hexane); $[\alpha]_D^{25} + 34.3° \pm 0.5°$ (c 1.00 CHCl$_3$); IR 1730 cm$^{-1}$ (acetate).

Anal. Calc. for C$_{47}$H$_{75}$O$_{10}$S: C, 67.75; H, 9.19; S, 3.85. Found: C, 67.92; H, 9.19; S, 3.85. 6-(Cholest-5-en-3β-yloxy)hexyl 2,3,4,6-tetra-O-acetyl-1-thio-β-D-galactopyranoside (VIa)

93% wax; $[\alpha]_D^{25} -23.0° \pm 0.5°$ (c 1.06 CHCl$_3$); IR 1740 cm$^{-1}$.

Anal. Calc. for C$_{47}$H$_{76}$O$_{10}$S: C, 67.75; H, 9.19; S, 3.85. Found: C, 67.89; H, 8.89; S, 3.77. Methyl [6-(cholest-5-en-3β-yloxy)hexyl 2,3,4-tri-O-acetyl-1-thio-β-D-glucopyranoside]uronate (VIc)

48%, needles (from 15% benzene in hexane), m.p. 144.5°-145° C.; $[\alpha]_D^{25} -42.9° \pm 0.5°$ (c 1.01 CHCl$_3$); IR 1735 (ester) cm$^{-1}$.

Anal. Calc. for C$_{47}$H$_{74}$O$_{10}$S: C, 67.45; H, 9.11; S, 3.91. Found: C, 67.68; H, 9.44; S, 4.20.

EXAMPLE 5

Process for deblocking of neutral glycolipids

A solution of 1 equivalent glycolipid in 1:1 ethanol-THF (33 ml per g substrate) was treated with 2.5-3 fold excess Bio-Rad AG 1-X2 OH$^-$ ion-exchange resin suspended in ethanol (16 ml per g substrate) and stirred 45 minutes at room temperature. The resin was filtered off and washed with warm THF (3×16 ml per g substrate), and the combined filtrates evaporated to give the following compounds:

6-(Cholest-5-en-3β-yloxy)hexyl 1-thio-α-D-mannopyranoside (VIIb)

91% colorless needles (from THF), d.s.c. endothermic transitions: 64-65 81-82, and 226°-227° C.; $[\alpha]_D^{25} + 77.9° \pm 0.9°$(c 1.11 THF); IR 3600–3100 (OH) cm$^{-1}$; (s), 1105 (s), 1070 (s) cm$^{-1}$; MS: 665 (M+), 501, 368.

Anal. Calc. for C$_{39}$H$_{68}$O$_6$S: C, 70.44, H, 10.31; S, 4.82. Found: C, 70.20; H, 10.22; S, 4.80.

6-(Cholest-5-en-3β-yloxy)hexyl 1-thio-β-D-galactopyranoside (VIIa)

66% pale tan powder, m.p. 104°-106° C. (to liquid crystal) and 219°-221° C. (to isotropic liquid); IR 3600-3100 (OH) cm$^{-1}$. Anal. Cal. for C$_{39}$H$_{68}$O$_6$S: C, 70.44; H, 10.31; S, 4.82. Found: C, 70.16; H, 10.03; S, 4.79.

[6-(Cholest-5-en-3β-yloxy)hexyl 1-thio-β-D-glucopyranosid]uronic acid (VIIc)

A solution of 30.2 mg (39.1 μmol) esterified glycolipid VIc in 2.0 ml 1:1 methanol-THF containing 20 μl H$_2$O was treated with 7.4 mg. (137 μmol) NaOCH$_3$ and stirred 3 hours at 25° C. The mixture was treated with 60 μl 2.5 N HCl (10% excess), evaporated, taken up in THF, and filtered. Evaporation of THF left 13.7 mg (52%) white powder, m.p. 104°-107° C.;IR 3600-2800 (RCOOH), 1745 and 1728 (RCOOH) cm$^{-1}$; field desorption MS: 701 (M+, Na+ salt). A 1 mg sample was per-O-trimethylsilylated with bis(trimethylsilyl)trifluoroacetamide at 25° C. in DMF and analyzed by MS: 967 (M+), 942, 874, 859, 501, 465. High resolution MS: Calc. for C$_{33}$H$_{57}$OS+: 501.4126; Found: 501,4126; Calc. for C$_{18}$H$_{41}$O$_6$Si$_4$+: 465.1982Found: 465.1965.

Anal. Calc. for C$_{39}$H$_{66}$O$_7$S: C, 68.99, H, 9.79; S, 4.72. Found: C, 69.48; H, 9.59; S, 4.65.

EXAMPLE 6

Preparation of 2,3,4-tri-O-acetyl-6-O-methylsulfonyl-α-D-mannopyranosyl Bromide An ice-cold solution of 14.9 g (34.9 mmol) 1,2,3,4-tetra-O-acetyl-6-O-methylsulfonyl-β-D-mannopyranose prepared by the process set forth in J. Fernandez-Bolanos and R. G. Fernandez-Bolanos, *An. Quim.*, 65 (1969) 1163-1164; *Chem. Abstr.*, 72 (1970) 133105w in 60 ml dry CH$_2$Cl$_2$ was treated with 21 ml 30-32% HBr in glacial AcOH, and kept 2.5 hours at 25° C. The mixture was poured into 400 ml stirred ice water, separated, and the aqueous phase washed with three 20 ml aliquots of CH$_2$Cl$_2$. The combined organic layers were washed with water and saturated NaHCO$_3$, dried with Na$_2$SO$_4$, evaporated, triturated with petroleum ether (bp 30°-60° C.), filtered, and air dried to leave 14.6 g (93%) of the solid α-glycosyl bromide IX, m.p. 167.5°-168.5° C. (dec); $[\alpha]_D^{25} + 120.0° \pm 0.5°$ (c 1.01 CHCl$_3$); IR 1740 and 1725 (acetate) cm$^{-1}$.

Anal. Calc. for C$_{13}$H$_{19}$BrO$_{10}$S: C, 34.91; H, 4.28; Br, 17.87; S, 7.17. Found: C, 35.04; H, 4.18; Br, 17.61; S, 7.27.

EXAMPLE 7

6-(Cholest-5-en-3β-yloxy)hexyl 2,3,4-tri-O-acetyl-6-azido-6-deoxy-1-thio-α-D-mannopyranoside (XIII)

The mannosyl bromide prepared by the process set forth in Example 6 was converted via the isothiouronium bromide X [85%, white powder, m.p. 87°–90° C. (dec); IR 3600–3100, 1740, 1640 cm$^{-1}$] to the corresponding thiol XI [89% colorless glass, IR 2560, 1750–1730 cm$^{-1}$] according to the process set forth in M. Cerny, J. Stanek and J. Pacak, Monatsh. 94 290–294 (1963). The thiol XI was coupled with IV as in Example 4 to provide 61% 6-(cholest-5-en-3β-yloxy)hexyl 2,3,4-tri-O-acetyl-6-D-methylsulfonyl-1-thio-α-D-mannopyranoside (XIII), a white glass, IR 1740 cm$^{-1}$. Finally, 1.14 g (1.32 mmol) of the preceding mesylate, 0.49 g (7.5 mmol) NaN$_3$, and 40 ml dry DMF were stirred together at 70°–75° C. under N$_2$ for 4.5 hours. After evaporating the solvent, the residue was dissolved in 20 ml ether, washed with three 10 ml portions of H$_2$O, dried with MgSO$_4$, and evaporated to leave 1.05 g (97%) title azide XIII as a colorless glass, homogenous on TLC (12% EtOAc in benzene on silica gel), $[\alpha]_D^{25}$ +12.6°±0.5° (c 1.02 CHCl$_3$); IR 2095 (azide), and 1755 (acetate) cm$^{-1}$. A 0.54 g sample was further purified by column chromatography (silica gel, 12% EtOAc in benzene), providing 0.417 g (75% yield), colorless glass which solidifed on prolonged standing, m.p. 68°–70° C.

Anal. Calc. for C$_{45}$H$_{73}$N$_3$O$_8$S: C, 66.22; H, 9.02; N, 5.15; S, 3.93. Found: C, 66.53; H, 8.98; N, 5.04; S, 3.98.

EXAMPLE 8

Preparation of 6-(Cholest-5-en-3β-yloxy)hexyl 6-azido-6-deoxy-1-thio-α-D-mannopyranoside (XIV)

Azido triacetate XIII was deblocked by the process set forth in Example 5 to provide 62% of the title azido triol XIV as a glass, IR 3600–3100 (OH), 2095 (azide) cm$^{-1}$.

Anal. Calc. for C$_{39}$H$_{67}$N$_3$O$_5$S: C, 67.88; H, 9.79; S, 4.65. Found C, 67.80; H, 9.55; S, 4.54.

EXAMPLE 9

Preparation of 6-(Cholest-5-en-3β-yloxy)hexyl 6-amino-6-deoxy-1-thio-α-D-mannopyranoside (VIId)

A solution of 0.163 g (0.236 mmol) of the azido triol prepared by the process set forth in Example 8 in 4.0 ml CHCl$_3$ containing 3.0 ml triethylamine was treated with dry gaseous H$_2$S at room temperature for 4.5 hours. The volatile components were removed by rotary evaporation and the product isolated by preparative TLC (silica gel, 7:2:1 CHCl$_3$/CH$_3$OH/conc. aqueous NH$_3$) to yield 65.0 mg (41%) white powder, m.p. indef.; IR 3650 (NH$_2$), 3600–3100 (OH) cm$^{-1}$; MS: 635 (M$^+$–CH$_2$=NH$^+$), 503, 470, 386, 368, 353. A 1 mg sample was per-O-trimethylsilylated with bis(trimethylsilyl)trifluoroacetamide in DMF at 65°–70° C. for 15 minutes, MS: 1024 (M$^+$), 1009, 951 (M$^+$–TMS), 936, 921, 850 [M$^+$–N(Si[CH$_3$]$_3$)$_2$, 523, 501, 368, 174 (base peak). A high resolution MS of the per-O-trimethylsilylated saccharide fragment was taken. Anal. Calc. for C$_{21}$H$_{52}$NO$_4$Si$_5$$^+$: 522.2744. Found 522.2721.

EXAMPLE 10

An aqueous suspension of the final product of formula VIIa in PBS in sterile filtered and added in levels of 0.005 mg and 0.05 mg to 2 samples of bivalent whole influenza vaccine (A Victoria and B Hong Kong strains). Similar adjuvant vaccine preparations are prepared using the final products of formula VIIb, VIIc and VIId.

EXAMPLE 11

The procedure of Example 10 is repeated using subunit A Victoria influenza vaccine.

What is claimed is:

1. A compound of the formula

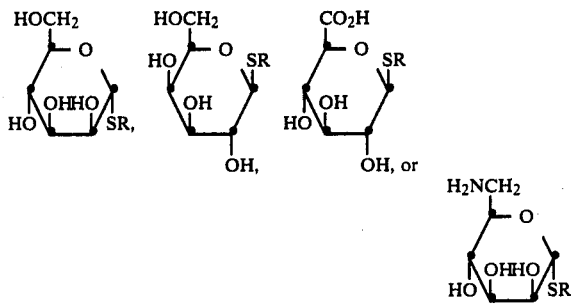

wherein R is

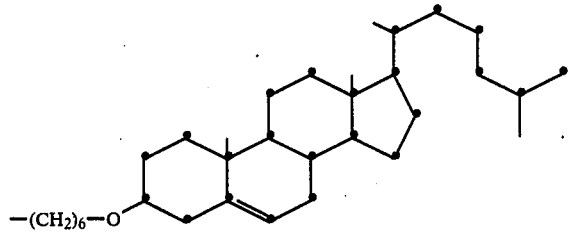

2. A compound of the formula:

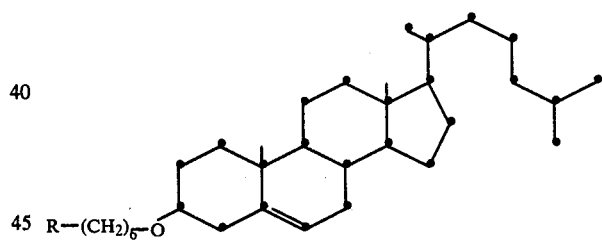

wherein R is OH, p-toluenesulfonyloxy, I,

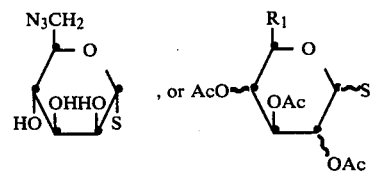

wherein R$_1$ is

methanesulfonyl, or N$_3$, AcO being acetyl.

3. A composition comprising an antigenic material and a compound of claim 1.

4. A composition according to claim 3 wherein the compound is present in an amount effective to exert an adjuvant effect.

* * * * *